United States Patent [19]

Lombard

[11] 4,232,020

[45] Nov. 4, 1980

[54] PROCESS FOR THE TREATMENT OF CHILDREN SUFFERING FROM A HYPERKINETIC SYNDROME

[75] Inventor: Jean-Pierre Lombard, Massy, France

[73] Assignee: C M Industries, France

[21] Appl. No.: 34,970

[22] Filed: May 1, 1979

[51] Int. Cl.² ............................................. A61K 27/00
[52] U.S. Cl. ................................................ 424/248.56
[58] Field of Search ................................... 424/248.56

[56] References Cited

PUBLICATIONS

Ornellas, Biochemistry & Pharm., vol. 20, pp. 2141–2147.
Laborit et al., Agressologie, (1969), 10 (10), pp. 469–478.

*Primary Examiner*—Stanley J. Friedman
*Attorney, Agent, or Firm*—Bacon & Thomas

[57] ABSTRACT

The present invention relates to a treatment of the "hyperkinetic syndrome" in children, wherein a medicine containing between 50 and 200 mg of 3-morpholinoethylamino 4-methyl 6-phenylpyridazine is administered daily to patients, by oral route.

1 Claim, No Drawings

PROCESS FOR THE TREATMENT OF CHILDREN SUFFERING FROM A HYPERKINETIC SYNDROME

The U.S. Pat. No. 4,169,158, issued Sept. 25, 1979, from application Ser. No. 820,489, filed July 29, 1977, describes one pharmaceutical use of the compound 3-morpholinoethylamino 4-methyl 6-phenyl pyridazine and of the pharmaceutically acceptable salts thereof.

This consists in using the compound as an anti-depressant; but it is specified in said patent that this anti-depressive activity did show some remarkable characteristics in relation to the anti-depressive activity of known anti-depressants.

A first table in the said patent shows the results obtained in clinical tests carried out for a whole series of depressive conditions, such as symptomatic depressive conditions, psychastenia, schizophrenia, psychosomatic diseases occurring in periods of tiredness and strain, and hypochondriac psychosis.

A second Table gives the results observed after different clinical tests, and showing that many clinical signs which are the consequence of the depressive conditions of the treated patients, could be improved when the anti-depressant described hereinabove is used.

It has now been found that this same product, namely the 3-morpholinoethylamino 4-methyl 6-phenyl pyridazine or a pharmaceutically acceptable salt thereof (hereinafter designated as 30038) when administered orally, in doses varying between 50 and 200 mg of active substance per day, could be used for treating "hyperactive children".

"Hyperactive children", i.e. children suffering from a "hyperkinetic syndrome" are described for example in the article written by P. H. WENDER of LIPTON M.A. et al. Psychopharmacology-A. Generation of Progress. Another analysis of the symptomatology of this syndrome is given by J. S. MILLER, Pediatrics Vol. 61, pages 217–223 (1978).

A description of the major symptoms of the syndrome is given for example in Table 2, page 1430 of the aforesaid work of LIPTON; these symptoms are also mentioned by J. S. MILLER in his aforesaid article.

It is surprising to note that "hyperactive children" such as defined above may be advantageously treated by the 3-morpholinoethylamino 4-methyl 6-phenyl pyridazine (30038), which had been described as having anti-depressive properties, since the prevailing symptoms noted in hyperactive children are the opposite of the symptoms which lead to a diagnosis of depression. Indeed, the hyperactive syndrome essentially comprises the following signs:

psychomotor excitability
agressivity
irritability
automatic opposition of antagonistic
muscles to passive movements (oppositionism).

Until now, hyperactive children have been treated in most cases with amphetamine substances which have the disadvantages of having important side-effects, of toxicity and risks of toxicomania.

The observations reported hereinafter correspond to a clinical study carried out in pediatrics according to the method of the crossed double blind test; patients are given at random:

either, a first therapeutical period of four weeks at a dose of 50 mg of 30038 in the morning and 50 mg of 30038 at night, followed immediately by a second four-week period consisting in the administering of placebo tablets at the same daily dose;

or, the reverse, a first four-week sequence using the placebo, followed immediately by a second four-week sequence with the aforesaid daily doses of 30038.

Purely by chance, 3 hyperactive children (obs. Nos. 3, 7 and 16) were treated first with the 30038 (first four weeks of the test), and then with the placebo-non active product for the 4 following weeks. On the contrary, 5 children (obs. Nos. 5, 10, 11, 19 and 20) were treated first with the placebo—first four weeks of the treatment—then with the 30038—the following four weeks.

The main characteristic symptoms of the hyperactive syndrome have been grouped in a scale of 8 symptoms (items).

The children were examined and questioned, on the day before the beginning of the treatment (day 0) as well as on the 14th day, on the 28th day (end of the first period of treatment with one of the two products), on the 42nd day and on the 56th day (end of the second period of treatment with the other product). The aforesaid scale of valuations was filled-in at each of the aforesaid interviews and for each child.

The gravity of each symptom (item) was rated with the following score:

0 = no symptom
1 = slight symptom
2 = symptom of average intensity
3 = symptom of strong intensity
4 = symptom of very strong intensity.

The total of the scores obtained and the average total score (total divided by the number of symptoms) were compared so as to determine, quantitatively, the improvement (or aggravation) of the hyperkinetic disease during the treatment by either one of the two products; by comparing the percentage of improvement in the scores at the end of each of the two periods of treatment for the same child, it is possible to determine the suitable therapeutic effect of the 30038 and to compare it with the effect of the inactive substance (Placebo). Indeed, all the tests of clinical psychopharmacology show that the placebo can entail a slight favourable effect in a number of patients, but this effect, which is not lasting, still remains clearly inferior to the favorable effect which can be attributed to a drug known to be active vis-à-vis the disease under study.

If the improvement in the average score at the end of the treatment with the 30038 is found to be clearly superior to the slight improvement which may be noted when the Placebo is administered, then it can be said that the 30038 is specifically efficient in hyperkinetic disorders. And this is noted from the 8 observations reported hereunder.

The characteristic symptoms in a hyperkinetic child, noted in the scale of valuations of this test are as follows:

1. Agressivity
2. Irritability
3. Oppositionism
4. Relational difficulties
5. Verbal and ideatory excitation
6. Anxiety
7. Fears
6. Sleep perturbed by terrors.

The results obtained are summed up in Table I.

These results indicate by what percentage the total score of gravity of the disease (initial score taken at 100%) has reduced (improvement) or increased (aggravation) at the end of the treatment period using the 30038 and at the end of the Placebo treatment.

TABLE I

| Obs. No. | Treatment with 30038 | Treatment with Placebo |
|---|---|---|
| | 30038 administered in 1st period(1st day to 27th day) | Placebo administered in 2nd period (28th to 56th day) |
| 03 | 37.0% of improvement | 22.0% of improvement |
| 07 | 42.6% of improvement | 21.3% of improvement |
| 16 | 48.4% of improvement | 2.9% of improvement |
| | 30038 administered 2nd period (28th to 56th day) | Placebo administered in 1st period (1st day to 27th day) |
| 05 | 44.9% of improvement | 0.0% unchanged |
| 10 | 59.2% of improvement | 18.4% of improvement |
| 11 | 65.6% of improvement | +4.3% of AGGRAVATION |
| 19 | 58.3% of improvement | 0.0% unchanged |
| 20 | 87.7% of improvement | 8.3% of improvement |
| Aver. out of 8 cases | 55.4% of improvement | 8.5% of improvement |

These results show:
for the 30038: a 55.4% improvement of the disease
for the Placebo: an 8.5% improvement of the disease (with one case of aggravation).

The results reported in Table I come from actual observations summed up hereunder:

Observation 3:

| Identification | : A.C. | Treatment duration : 8 weeks |
|---|---|---|
| Sex | : Male | |
| Age | : 15 | |
| Height | : 150 cm | |
| Weight | : 45 kg | |

Diagnosis : Hyperactive syndrome
Previous treatment : none
Treatment from the 1st day to the 27th day:    30038-one 50 mg tablet morning and evening
Treatment from the 28th day to the 56th day:    1 tablet of Placebo morning and evening Initial gravity of disease: the syndrome is severe since it corresponds to an average score of 2.91 before treatment.

| | Evolution of the syndrome | | | | |
|---|---|---|---|---|---|
| | Day 0 Initial state | 14th day | 28th day | 42nd day | 56th day |
| Average total score | 2.91 | 1.82 | 1.82 | 2.18 | 2.27 |
| % of improvement | — | 37.5% | 37.5% | 25.1% | 22.0% |
| | | 30038 | | PLACEBO | |

Observation 7:

| Identification | : J.D. | Treatment duration: 8 weeks |
|---|---|---|
| Sex | : Male | |
| Age | : 15 | |
| Height | : 157 cm | |
| Weight | : 45 kg | |

Diagnosis: Hyperactive syndrome
Previous treatment: none
Treatment from the 1st day to the 27th day :    30038-one 50 mg tablet morning and evening.
Treatment from the 28th day to the 56th day:    one tablet of Placebo morning and evening Initial gravity of the disease: the condition of the patient is of average gravity since the average total score is 1.27 before treament.

| | Evolution of the syndrome: | | | | |
|---|---|---|---|---|---|
| | Day 0 Initial state | 14th day | 28th day | 42nd day | 56th day |
| Average total score | 1.27 | 1.27 | 0.73 | 1.00 | 1.00 |
| % of improvement | — | 0.00% | 42.6% | 21.3% | 21.3% |
| | | 30038 | | PLACEBO | |

Observation 16:

| Identification | : C.B. | Treatment duration: 8 weeks |
|---|---|---|
| Sex | : Male | |
| Age | : 15 | |
| Height | : 169 cm | |
| Weight | : 56.5 kg | |

Diagnosis : Hyperactive syndrome
Previous treatment: none
Treatment from the 1st day to the 27th day:    30038 - one 50 mg tablet morning and evening
Treatment from the 28th day to the 56th day:    one Placebo tablet, morning and evening Initial gravity of the disease: This is a severe case since the average total score is 2.81 before the start of the treatment. Very aggressive and irritable child, strong attitude of opposition and great relational difficulty. The symptoms of anxiety and perturbed sleep are also important.

| | Evolution of the syndrome | | | | |
|---|---|---|---|---|---|
| | Day 0 Initial state | 14th day | 28th day | 42nd day | 56th day |
| Average total score | 2.81 | 2.09 | 1.45 | 1.63 | 2.73 |
| % of improvement | — | 25.7% | 48.4% | 42.0% | 2.9% |
| | | 30038 | | PLACEBO | |

Observation 5:

| Identification | : J.L. | Treatment duration: 8 weeks |
|---|---|---|
| Sex | : Male | |
| Age | : 15 | |
| Height | : 161 cm | |
| Weight | : 58 kg | |

Diagnosis: Hyperactive syndrome
Previous treatment: none
Treatment from the 1st day to the 27th day:    one Placebo tablet, morning and evening
Treatment from the 28th day to the 56th day:    30038 - one 50 mg
                                                    tablet
                                                    morning
                                                    and
                                                    evening Initial gravity of the disease: Very hyperactive subject with a high degree of aggressivity, irritability and oppositionism. The symptoms normally accompanying the hyperactive syndrome (anxiety, etc..) are present and important.

Evolution of the syndrome

|  | Day 0 Initial state | 14th day | 28th day | 42nd day | 56th day |
|---|---|---|---|---|---|
| Average total score | 2.63 | 2.63 | 2.63 | 2.27 | 1.45 |
| % of improvement | — | 0.00% | 0.00% | 13.7% | 44.9 |
|  |  | PLACEBO |  | 30038 |  |

Observation 10:

| Identification | : C.R. | Treatment duration : 8 weeks |
|---|---|---|
| Sex | : Male | |
| Age | : 15 | |
| Height | : 165 cm | |
| Weight | : 47.5 kg | |

Diagnosis : Hyperactive syndrome
Previous treatment: none
Treatment from the 1st day to the 27th day:    one Placebo tablet, morning and evening
Treatment from the 28th day to the 56th day:  30038 - one 50 mg tablet morning and evening Initial gravity of the disease: The initial symptomatology is strong for all the most characteristic signs of the syndrome (aggressivity, irritability, oppositionism, relational difficulty, verbal and ideatory excitation).

Evolution of the syndrome:

|  | Day 0 Initial state | 14th day | 28th day | 42nd day | 56th day |
|---|---|---|---|---|---|
| Average total score | 2.45 | 2.45 | 2.00 | 1.00 | 1.00 |
| % of improvement | — | 0.00% | 18.4% | 59.2% | 59.2% |
|  |  | PLACEBO |  | 30038 |  |

Observation 11:

| Identification | : A.G. | Treatment Duration : 8 weeks |
|---|---|---|
| Sex | : Male | |
| Age | : 15 | |
| Height | : 156 cm | |
| Weight | : 56 kg | |

Diagnosis : Hyperactive syndrome
Previous treatment: None
Treatment from the 1st day to the 27th day:    one Placebo tablet morning and evening.
Treatment from the 28th day to the 56th day:  30038 - one 50 mg tablet morning and evening Initial gravity of the disease: the total symptomatology is of average intensity (initial average score: 2.09) but the most characteristic symptoms are clearly found (in particular as far as verbal and ideatory excitation and relational difficulties are concerned).

Evolution of the syndrome:

|  | Day 0 Initial state | 14th day | 28th day | 42nd day | 56th day |
|---|---|---|---|---|---|
| Average total score | 2.09 | 2.18 | 2.18 | 1.18 | 0.72 |
| % of improvement | — | +4.3% | +4.3% | 43.6% | 65.6% |
|  |  | PLACEBO |  | 30038 |  |

Observation 19

| Identification | : N.P. | Treatment duration: 8 weeks |
|---|---|---|
| Sex | : Male | |
| Age | : 13 | |
| Height | : 140 cm | |
| Weight | : 46 kg | |

Diagnosis : Hyperactive syndrome
Previous treatment: none
Treatment from the 1st to the 27th day:    1 Placebo tablet morning and evening.
Treatment from the 28th to the 56th day:  30038 one 50 mg tablet, morning and evening Initial gravity of the disease: The total symptomatology indicates an average gravity (initial average total score: 2.18). The main symptoms of the hyperactive clinical table are found and in particular the symptoms of irritability and of verbal and ideatory excitation are noted (rated : 3). The aggressivity and relational difficulties are average in intensity. Other symptoms conventionally known to accompany infantile hyperactivity are of course present, often in very strong proportions.

Evolution of the Syndrome

|  | Day 0 Initial state | 14th day | 28th day | 42nd day | 56th day |
|---|---|---|---|---|---|
| Average total score | 2.18 | 1.63 | 2.18 | 1.36 | 0.91 |
| % of improvement | — | 25.3% | 0.0% | 37.7% | 48.3% |
|  |  | PLACEBO |  | 30038 |  |

Observation 20:

| Identification | : O.R. | Treatment duration: 8 weeks |
|---|---|---|
| Sex | :Male | |
| Age | : 13 | |
| Height | : 146 cm | |
| Weight | : 42 kg | |

Diagnosis: Hyperactive syndrome
Previous treatment: none
Treatment from the 1st day to the 27th day:    one Placebo tablet, morning and evening
Treatment from the 28th day to the 56th day:  30038 - one 50 mg tablet morning and evening Initial gravity of the disease: The intensity of the overall symptomatology is average (initial average total score: 2.18). The main target symptoms of the hyperactive syndrome are noted, and in particular, -continued aggressivity and irritability are present in a high proportion. Most of the other symptoms are also found, and in some cases, in very high proportions.

Evolution of the Syndrome:

|  | Day 0 Initial state | 14th day | 28th day | 42nd day | 56th day |
|---|---|---|---|---|---|
| Average total score | 2.18 | 2.18 | 2.00 | 0.54 | 0.27 |
| % of improvement | — | 0.0% | 8.3% | 75.3% | 87.7% |

-continued

| PLACEBO | 30038 |
|---|---|

No side-effects have been found to result from the administering of 30038, whether during or after the treatments.

What is claimed is:

1. A method for the treatment of hyperkinetic syndrome in children, comprising orally administering daily to the hyperactive child from 50 mg to 200 mg of 3-morpholinoethylamino-4-methyl-6-phenylpyridazine or a pharmaceutically acceptable salt thereof.

* * * * *